(12) United States Patent
Haenel et al.

(10) Patent No.: US 12,188,641 B2
(45) Date of Patent: *Jan. 7, 2025

(54) YOKE FOR A SUSPENSION SYSTEM FOR A MEDICAL LAMP

(71) Applicant: TRUMPF MEDIZIN SYSTEME GMBH + CO. KG, Saalfeld (DE)

(72) Inventors: Martin Haenel, Saalfeld (DE); Lars Hanuschka, Saalfeld (DE)

(73) Assignee: TRUMPE MEDIZIN SYSTEME GMBH + CO. KG, Saalfeld (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/530,882

(22) Filed: Dec. 6, 2023

(65) Prior Publication Data

US 2024/0102623 A1    Mar. 28, 2024

Related U.S. Application Data

(63) Continuation of application No. 17/715,231, filed on Apr. 7, 2022, now Pat. No. 11,920,759.

(30) Foreign Application Priority Data

Apr. 9, 2021    (EP) .................................... 21167648

(51) Int. Cl.
*F21V 21/26*     (2006.01)
*A61B 90/35*     (2016.01)
*F16M 11/20*     (2006.01)
*F21W 131/205*   (2006.01)

(52) U.S. Cl.
CPC .............. *F21V 21/26* (2013.01); *A61B 90/35* (2016.02); *F16M 11/2057* (2013.01); *F21W 2131/205* (2013.01)

(58) Field of Classification Search
CPC .......... F21V 21/26; F16M 11/20; A61B 90/35
See application file for complete search history.

(56) References Cited

U.S. PATENT DOCUMENTS

| | | |
|---|---|---|
| 860,303 A | 7/1907 | Jones |
| 1,686,341 A | 10/1928 | Nathanson |
| 2,287,577 A | 6/1942 | Stava |
| 2,547,532 A | 4/1951 | Mendelsohn |
| 2,911,519 A | 11/1959 | Phillips et al. |
| 2,941,776 A | 6/1960 | Lauterbach |
| 3,000,606 A | 9/1961 | Storm, Jr. et al. |
| 3,010,013 A | 11/1961 | Gunther et al. |
| 3,012,781 A | 12/1961 | Nelson |
| 3,240,925 A | 3/1966 | Paschke et al. |
| 3,272,928 A | 9/1966 | Hainzelin |
| 3,360,640 A | 12/1967 | Seitz et al. |

(Continued)

*Primary Examiner* — Alexander K Garlen

(74) *Attorney, Agent, or Firm* — Barnes & Thornburg LLP

(57) ABSTRACT

A yoke for a suspension system for a medical lamp comprises a rigid yoke member having a first end and a second end, a first revolving joint-component fixed to the first end, wherein the first revolving joint has a first rotation axis, and a second revolving joint-component fixed to the second end, wherein the second revolving joint has a second rotation axis. The first rotation axis is included in a plane and the second rotation axis intersects the plane or is included in the plane, and the first rotation axis and a projection, onto the plane, of the second rotation axis intersecting the plane or the second rotation axis included in the plane enclose an angle ($\alpha$) of more than 0 degrees and less than 90 degrees.

19 Claims, 4 Drawing Sheets

(56) References Cited

U.S. PATENT DOCUMENTS

| | | |
|---|---|---|
| 3,584,793 A | 6/1971 | Ilzig et al. |
| 3,783,262 A | 1/1974 | Pile |
| 3,820,752 A | 6/1974 | Oram |
| 3,936,671 A | 2/1976 | Bobrick et al. |
| 4,032,775 A | 6/1977 | Bobrick et al. |
| 4,080,530 A | 3/1978 | Krogsrud |
| 4,082,244 A | 4/1978 | Groff |
| 4,097,919 A | 6/1978 | Bobrick et al. |
| 4,107,769 A | 8/1978 | Saluja |
| 4,130,858 A | 12/1978 | Hayakawa |
| 4,160,536 A | 7/1979 | Krogsrud |
| 4,165,530 A | 8/1979 | Sowden |
| 4,166,602 A | 9/1979 | Gabel et al. |
| 4,208,028 A | 6/1980 | Brown et al. |
| 4,266,747 A | 5/1981 | Souder, Jr. et al. |
| 4,390,932 A | 6/1983 | Matsui et al. |
| 4,447,031 A | 5/1984 | Souder, Jr. et al. |
| 4,453,687 A | 6/1984 | Sweere |
| 4,494,177 A | 1/1985 | Matthews |
| 4,517,632 A | 5/1985 | Roos |
| 4,523,732 A | 6/1985 | Biber et al. |
| 4,692,849 A | 9/1987 | Le Vantine |
| 4,744,019 A | 5/1988 | Krogsrud |
| 4,770,384 A | 9/1988 | Kuwazima et al. |
| 4,836,478 A | 6/1989 | Sweere |
| 4,844,387 A | 7/1989 | Sorgi et al. |
| 4,846,434 A | 7/1989 | Krogsrud |
| 4,953,822 A | 9/1990 | Sharber et al. |
| 5,025,359 A | 6/1991 | Saluja et al. |
| 5,038,261 A | 8/1991 | Kloos |
| 5,108,063 A | 4/1992 | Koerber, Sr. et al. |
| 5,165,786 A | 11/1992 | Hubert |
| 5,173,803 A | 12/1992 | Heller |
| 5,186,337 A | 2/1993 | Foster et al. |
| 5,277,427 A | 1/1994 | Bryan et al. |
| 5,333,103 A | 7/1994 | Cvek |
| 5,340,072 A | 8/1994 | Halbirt |
| 5,348,260 A | 9/1994 | Acevedo |
| 5,603,496 A | 2/1997 | Rappaport |
| 5,618,090 A | 4/1997 | Montague et al. |
| 5,826,846 A | 10/1998 | Buccieri et al. |
| 6,012,693 A | 1/2000 | Voeller et al. |
| 6,012,821 A | 1/2000 | Yeaney et al. |
| 6,132,062 A | 10/2000 | Borders et al. |
| 6,176,597 B1 | 1/2001 | Smith |
| 6,328,458 B1 | 12/2001 | Bell et al. |
| 6,402,351 B1 | 6/2002 | Borders et al. |
| 6,431,515 B1 | 8/2002 | Gampe et al. |
| 6,443,596 B1 | 9/2002 | Bulko et al. |
| 6,471,363 B2 | 10/2002 | Howell et al. |
| 6,639,623 B2 | 10/2003 | Howell et al. |
| 6,698,704 B2 | 3/2004 | Kuhn |
| 6,899,442 B2 | 5/2005 | Howell et al. |
| 7,726,823 B2 | 6/2010 | Rus et al. |
| 8,070,331 B2 | 12/2011 | Gull et al. |
| 10,993,778 B2 | 5/2021 | Bellows et al. |
| 11,920,759 B2 | 3/2024 | Haenel et al. |
| 2002/0139913 A1 | 10/2002 | Kummerfeld et al. |
| 2003/0021107 A1 | 1/2003 | Howell et al. |
| 2003/0094549 A1 | 5/2003 | Gaertner et al. |
| 2003/0160142 A1 | 8/2003 | Brahler et al. |
| 2003/0161159 A1 | 8/2003 | Kupfer |
| 2004/0188578 A1 | 9/2004 | Turner |
| 2004/0199996 A1 | 10/2004 | Newkirk et al. |
| 2005/0243720 A1 | 11/2005 | Rodewald et al. |
| 2007/0176060 A1 | 8/2007 | White et al. |
| 2009/0318770 A1 | 12/2009 | Marka et al. |
| 2011/0079697 A1 | 4/2011 | Mller et al. |
| 2014/0066722 A1 | 3/2014 | Marka et al. |
| 2017/0167702 A1 | 6/2017 | Mariampillai et al. |
| 2017/0241587 A1 | 8/2017 | Timoszyk |
| 2018/0238259 A1 | 8/2018 | Liang et al. |
| 2022/0166910 A1 | 5/2022 | Chang et al. |
| 2022/0325859 A1 | 10/2022 | Haenel et al. |

YOKE FOR A SUSPENSION SYSTEM FOR A MEDICAL LAMP

CROSS-REFERENCE TO RELATED APPLICATIONS

This application is a continuation of U.S. application Ser. No. 17/715,231 filed Apr. 7, 2022, which claims the benefit of European Patent Application Serial No. 21167648.1, filed Apr. 9, 2021, the entire disclosure of each of which is incorporated herein by reference in its entirety.

BACKGROUND

The present disclosure relates to a yoke for a suspension system for a medical lamp, the suspension system for the medical lamp and a system of a medical lamp body and the suspension system, in particular, for a medical lamp used as an examination lamp or a surgical lamp.

Medical lamps which are either installed to a ceiling of, e.g., an operating theater or a resuscitation room or to a stand in such a room are provided with a suspension system having at least one yoke having defined characteristics. At its ends, the yoke is provided with components of a respective revolving joint, wherein the rotation axes of the revolving joints enclose an angle of 90 degrees. By using the suspension system comprising one yoke having such characteristics, if the revolving joints are not provided with a stopper, any spatial angle of a lamp body can be reached. When using two of these yokes, any spatial angle can be reached more comfortable.

However, by using the suspension system having two yokes, wherein the rotation axes of the revolving joints of the yokes respectively enclose the angle of 90 degrees, particularly if the lamp body is provided with several control interfaces located along the circumference of the lamp body, the control interfaces can probably be hidden by the yoke when the lamp body is in a horizontal or almost horizontal posture which is quite usual for its use. Moreover, due to strength reasons, the yokes are made of steel and, therefore, their weight hampers in easy positioning of the lamp body as more as longer the yokes are. Finally, in the case of two yokes, for example in the case of yokes having the shape of a quarter circle, since the yokes have to move past each other, they need to have different radii and, furthermore, for adjusting a center of gravity of the lamp body which is usually at least almost in the geometric center of lamp body into the center of a rotational movement enabled by the yokes, two different yokes are necessary which increases manufacturing costs.

Therefore, the object underlying the present disclosure is to solve these above-mentioned problems and to provide a yoke which enables an easy operation of a medical lamp. The object is achieved by a yoke and suspension system according to present disclosure claims.

SUMMARY

The present disclosure includes one or more of the features recited in the appended claims and/or the following features which, alone or in any combination, may comprise patentable subject matter.

According to an aspect of the present disclosure, a yoke for a suspension system for a medical lamp is provided. The yoke comprises a rigid yoke member having a first end and a second end, at least one first revolving joint-component fixed to the first end, wherein the first revolving joint has a first rotation axis, and at least one second revolving joint-component fixed to the second end, wherein the second revolving joint has a second rotation axis. The first rotation axis is included in a plane and the second rotation axis intersects the plane or is included in the plane, and the first rotation axis and a projection, onto the plane, of the second rotation axis intersecting the plane or the second rotation axis included in the plane enclose an angle of more than 0 degrees and less than 90 degrees.

Such a yoke enables reaching any spatial postures of a lamp body while facilitating movement of the lamp body of the medical lamp due to less weight.

According to embodiments of the yoke, the first rotation axis and the second rotation axes or the projection of the second rotation axis enclose an angle of more than 15 degrees and less than 75 degrees, and in some embodiments, an angle of 60 degrees.

By selecting the angle in such a range, a good compromise between a reduction of the weight of the yoke and the operability of the lamp body can be found.

According to a further embodiment of the yoke, the rigid yoke member has a hollow cross section along its entire length.

By this feature, the weight of the yoke is further reduced so that the operability is further enhanced.

According to a yet further embodiment of the yoke, the yoke comprises an electrical equipment.

When comprising the electrical equipment, in particular, in the hollow cross section of the yoke member, the medical lamp body can be supplied with energy and/or data without deteriorating hygienic conditions.

Due to a further embodiment of the yoke, at least one of the first revolving joint and the second revolving joint is fixed as an entire assembly to the rigid yoke member and has a mechanical interface for being fixable to a further element.

In this implementation, either the lamp body or a face to which the yoke is fastened, for example a further arm of the suspension system, does not have to be provided with another component of the revolving joint so that a simple modular concept is achieved.

According to a further embodiment of the yoke, the at least one of the entire assembly of the first revolving joint and the second revolving joint comprises a brake device.

By providing the brake device, an unwanted motion of the lamp body can be prevented.

In a further embodiment of the yoke, the rigid yoke member is made by hydro forming.

Hydroforming provides the advantage that even complicated shapes of objects, here the rigid yoke member, are easily possible so that further functions can be integrated while having the possibility of providing an attractive shape.

According to a further aspect of the present disclosure, a suspension system for a medical lamp comprises two yokes, wherein at least one yoke is a yoke as described before.

By providing at least one of the before described yokes, the before-mentioned advantage of the reduction of the weight can be at least partially achieved.

In an embodiment of the suspension system, the suspension system comprises two of the before described yokes.

When using two of these yokes, all of the above-described disadvantages can be prevented so that facilitating access to a control interface and easy positioning are also enabled.

In a further embodiment of the suspension system, the rigid yoke members of the two yokes have identical shapes.

In this implementation, the production costs can be lowered since only one type of yoke is necessary and, therefore, the quantity of one type of articles is increased and the need of storing several different articles is prevented.

In a yet further embodiment of the suspension system, the revolving joint between the two yokes comprises a brake device.

By providing the brake device, an unwanted motion of the lamp body can be prevented.

According to a further aspect of the present disclosure, a system of a lamp body of a medical lamp and an above described suspension system is provided.

When using such a system, an easy access to a control interface and an easy positioning are additionally enabled.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
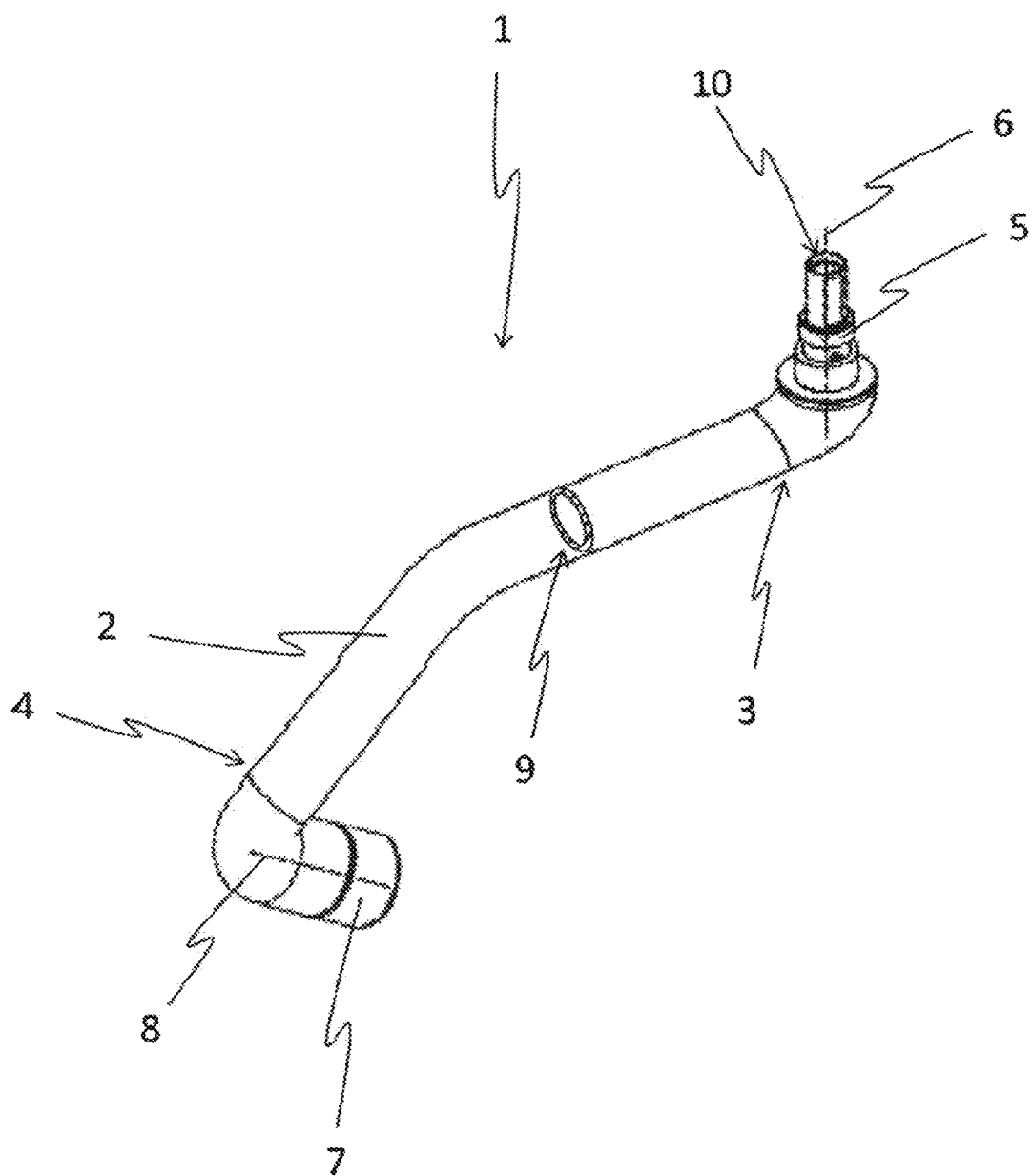
FIG. 1 shows a perspective view of a yoke according to the present disclosure.

FIG. 1 shows a perspective view of a yoke 1 according to the present disclosure. The yoke 1 comprises a rigid yoke member 2 having a first end 3 and a second end 4. Furthermore, to the first end 3, a first revolving joint-component 5 is fixed. The first revolving joint has a first rotation axis 6. To the second end 4, a second revolving joint-component 7 is fixed. The second revolving joint has a second rotation axis 8.

In alternative embodiments, not only a component of the first and second revolving joint is respectively fixed to the first end 3 and/or second end 4 of the rigid yoke member 2 but an entire assembly of a revolving joint is respectively fixed to the first end 3 and/or the second end 4. Such an assembly of a revolving joint optionally comprises a brake device.

The rigid yoke member 2 has a hollow cross section 9 along its entire length. The rigid yoke member 2 is made by hydroforming. In this manufacturing method, a blank in the form of, e.g., a tube, is processed by a fluid which is entered into a cavity of the blank. This cavity is formed by the inner bore of the tube which is closed except from an input line of the fluid. By high-pressure fluid inserted into the cavity, the tube is expanded and applies itself to an inner face of a mold in which the blank is arranged to generate a desired outer shape of the rigid yoke member 2. Alternatively, the rigid yoke member 2 is not made by hydroforming but conventionality bent tubes are used to which the components of the revolving joints are welded.

Furthermore, the yoke comprises an electrical equipment 10. This electrical equipment 10 comprises a flexible cable which is provided with connectors at its ends. These connectors are attached in the revolving joint-components 5, 7. In particular, the connectors are formed as components of sliding contacts to ensure a rotation of the rotating joints without stop.

Figure 2:
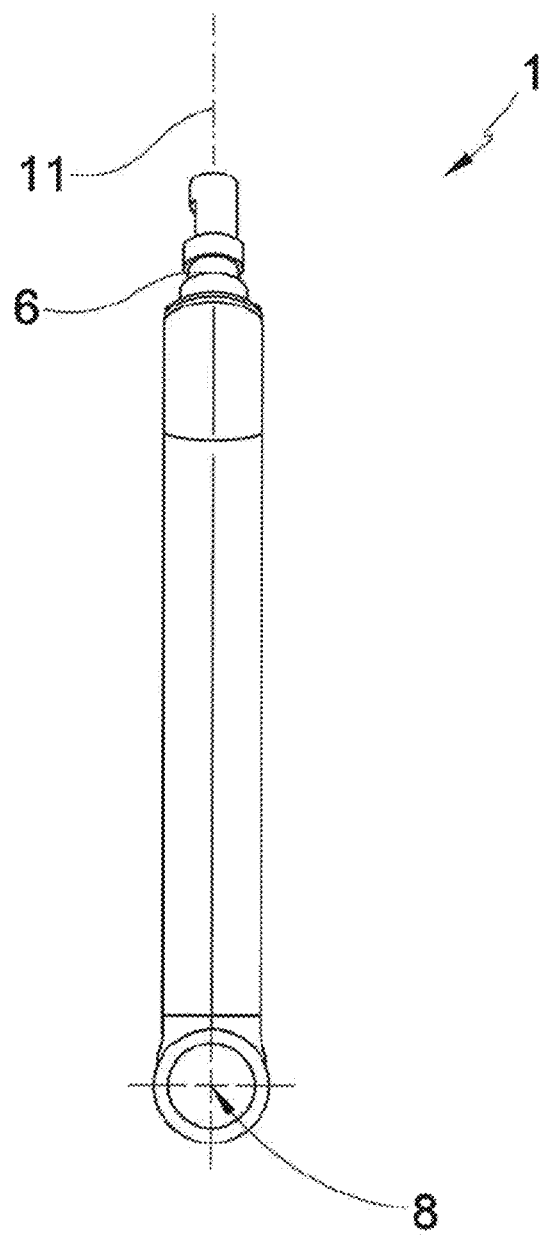
FIG. 2 shows a view on the yoke in a direction parallel to a plane including the first and second rotation axis.

FIG. 2 shows a view on the yoke 1 in a direction parallel to a plane 11 including the first rotation axis 6 and second rotation axis 8. In an alternative embodiment, the second rotation axis 8 is not included in the plane 11 but the second revolving joint is twisted with respect to the plane so that the second rotation axis 8 intersects the plane 11.

Figure 3:
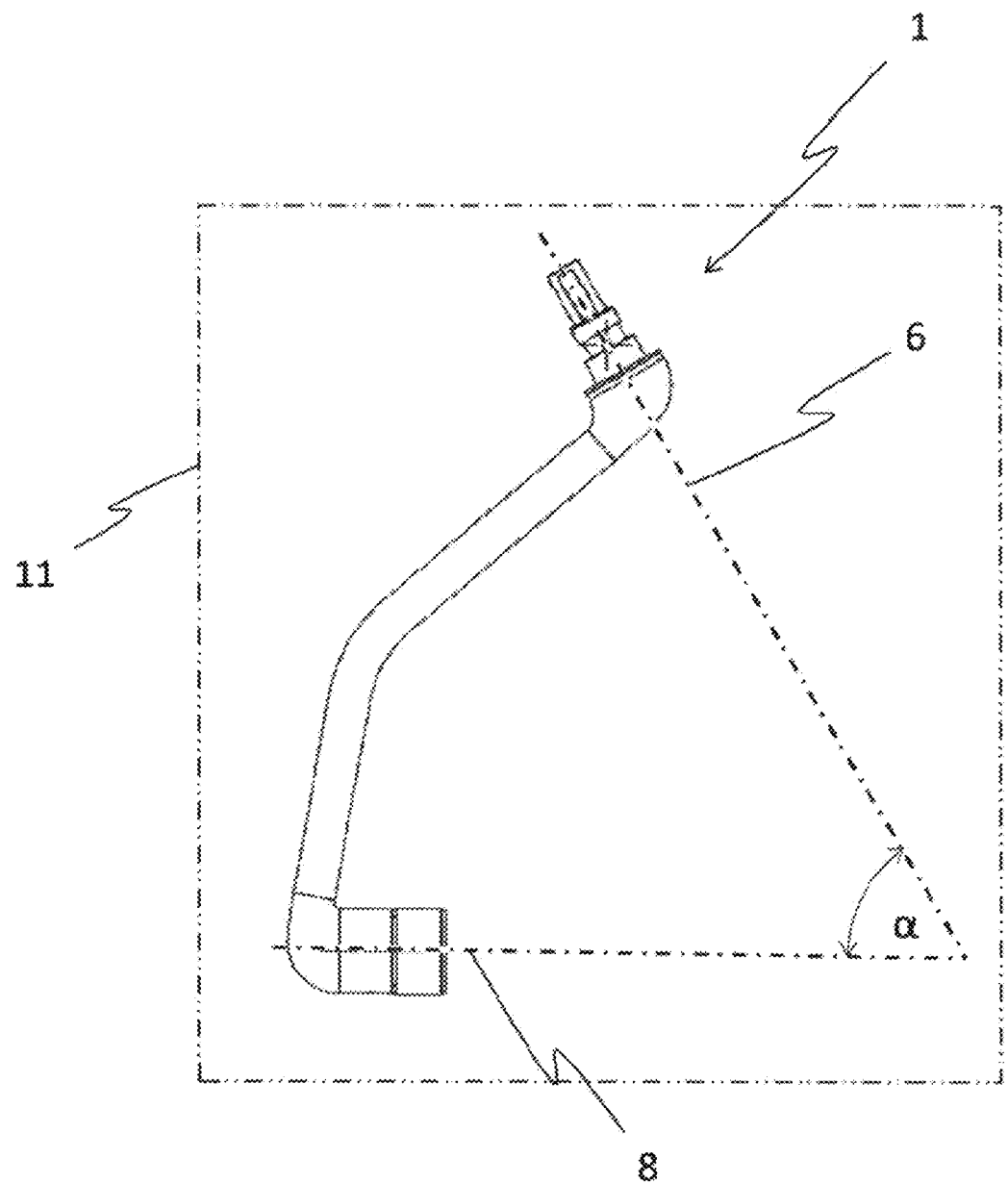
FIG. 3 shows a view on the yoke in a direction perpendicular to the plane.

FIG. 3 shows a view on the yoke 1 in a direction perpendicular to the plane 11. The first rotation axis 6 and the second rotation axis 8 both included in the plane 11 enclose an angle of 60 degrees. In alternative embodiments, the enclosed angle α is within a range of more than 0° and less than 90° or, and in some embodiments, in a range of more than 15° and less than 75°.

Figure 4:
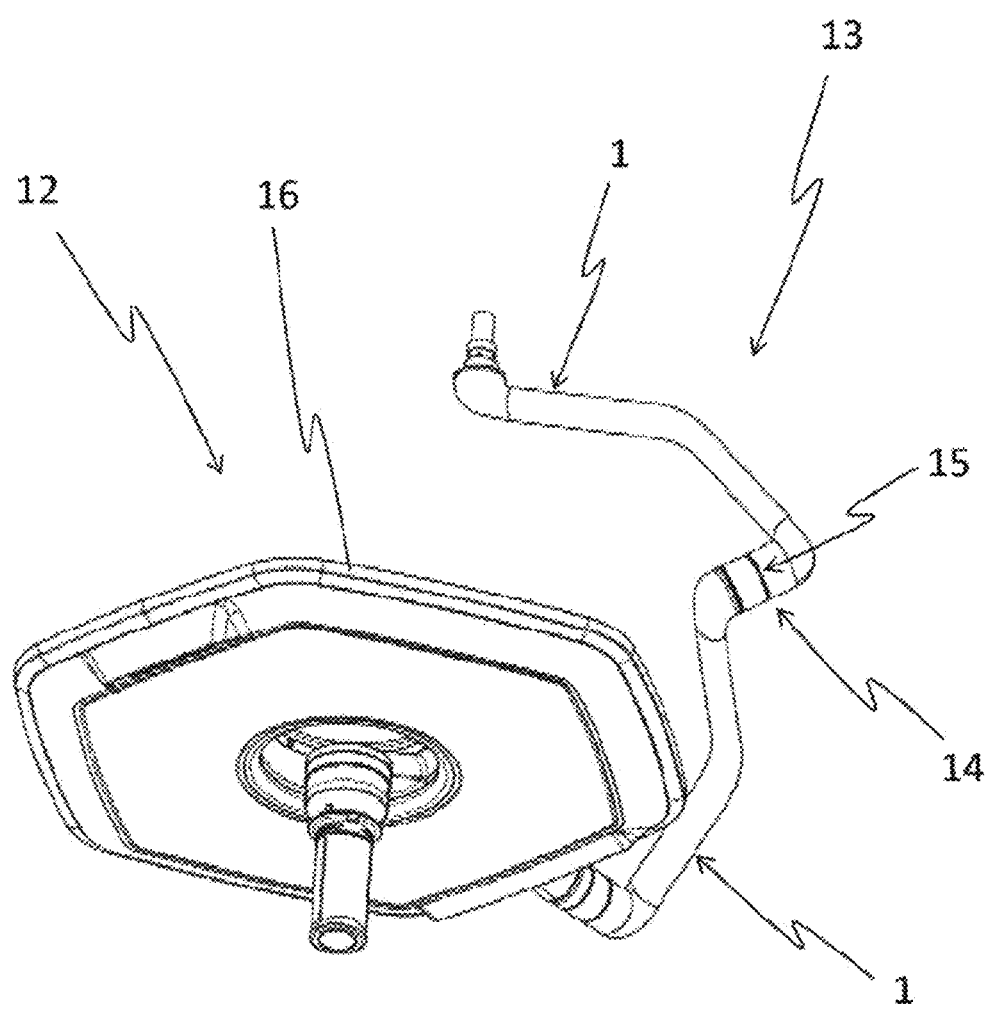
FIG. 4 shows a perspective view of a system of a lamp body of a surgical lamp and a suspension system provided with two yokes.

FIG. 4 shows a perspective view of a system of a medical lamp 12 comprising a lamp body 16 and a suspension system 13 provided with two of the yokes 1. In the shown embodiment, the medical lamp 12 is represented by a surgical lamp and the suspension system 13 comprises two yokes 1 having an identical shape. In alternative embodiments, the medical lamp 12 is, e.g., represented by an examination lamp, the suspension system 13 merely comprises one of the yokes 1 or comprises two of the yokes 1 having different shapes, also either having an enclosed angle by the first revolving joint and the second revolving joint in the above-mentioned range or having an arbitrary shape.

The revolving joint 14 between the two yokes 1 is provided with a brake device 15. In an alternative embodiment, the revolving joint 14 is not provided with the brake device 15 but a lock of a posture of the two yokes 1 is achieved by another measure, for example, sluggishness of the revolving joint 14.

In use, the lamp body 16 of the medical lamp 12, suspended by the suspension system 13 is moved manually into an arbitrary spatial posture. Thereby, the two yokes 1 can move past each other, wherein, due to the respectively selected angle α between the first rotation axis 6 and the second rotation axis 8, in an almost horizontal posture of the lamp body 16, the revolving joint 14 between the two yokes 1 is located above a lamp body 16 of the medical lamp 12. Therefore, a control interface provided at any location at the circumference of the lamp body 16 would not be hidden by the suspension system 13. Moreover, since the revolving joint 14 between the two yokes 1 is located at a greater height with respect to the floor, compared to conventional suspension systems having two yokes, the rotation axes of which enclose 90 degrees, more free space above a location of operation of the medical lamp 12 is achieved.

Moreover, since a length of the yokes 1 is reduced with respect to conventional suspension systems, a mass to be moved is reduced and, therefore, an operation force is lower than in the case of the conventional suspension system.

While the disclosure has been illustrated and described in detail in the drawings and the foregoing description, such illustration and description are to be considered illustrative or exemplary and not restrictive. The disclosure is not limited to the disclosed embodiments. From reading the present disclosure, other modifications will be apparent to a person skilled in the art. Such modifications may involve other features, which are already known in the art and may be used instead of or in addition to features already described herein. In the claims, the word "comprising" does not exclude other elements or steps, and the indefinite article "a" or "an" does not exclude a plurality.

Although this disclosure refers to specific embodiments, it will be understood by those skilled in the art that various changes in form and detail may be made without departing from the subject matter set forth in the accompanying claims.

The invention claimed is:

1. A suspension system for a medical lamp comprising:
at least two yokes, a first yoke including
a yoke member having a first end and a second end,
a first revolving joint at the first end, the first revolving joint having a first rotation axis, and
a second revolving joint at the second end, the second revolving joint having a second rotation axis,
wherein the first rotation axis is included in a plane and the second rotation axis is not included in the plane,
the first rotation axis and a projection, perpendicularly projected onto the plane, of the second rotation axis encloses an angle ($\alpha$) of more than 0 degrees and less than 90 degrees.

2. The suspension system of claim 1, wherein the first rotation axis and the projection of the second rotation axis enclose the angle ($\alpha$) of more than 15 degrees and less than 75 degrees.

3. The suspension system of claim 2, wherein the first rotation axis and the projection of the second rotation axis enclose the angle ($\alpha$) of 60 degrees.

4. The suspension system of claim 1, wherein the first rotation axis and the projection of the second rotation axis enclose the angle ($\alpha$) of 60 degrees.

5. The suspension system of claim 1, wherein the yoke member has a hollow cross section along its entire length.

6. The suspension system of claim 5, wherein the yoke comprises electrical equipment.

7. The suspension system of claim 6, wherein at least one of the first revolving joint and the second revolving joint is fixed as an entire assembly to the yoke member and the entire assembly has a mechanical interface for being fixable to a further element.

8. The suspension system of claim 7, wherein the at least one of the entire assembly of the first revolving joint and the second revolving joint comprises a brake device.

9. The suspension system of claim 1, wherein at least one of the first revolving joint and the second revolving joint is fixed as an entire assembly to the yoke member and the entire assembly has a mechanical interface for being fixable to a further element.

10. The suspension system of claim 9, wherein the at least one of the entire assembly of the first revolving joint and the second revolving joint comprises a brake device.

11. The suspension system of claim 1, wherein the at least one of the entire assembly of the first revolving joint and the second revolving joint comprises a brake device.

12. The suspension system of claim 1, wherein the yoke member is made by hydroforming.

13. The suspension system of claim 1, wherein a second yoke of the at least two yokes includes:
a yoke member having a first end and a second end,
a first revolving joint at the first end, the first revolving joint having a first rotation axis, and
a second revolving joint fixed to at the second end, the second revolving joint having a second rotation axis,
wherein the first rotation axis is included in a plane and the second rotation axis is not included in the plane,
the first rotation axis and a projection, perpendicularly projected onto the plane, of the second rotation axis encloses an angle ($\alpha$) of more than 0 degrees and less than 90 degrees.

14. The suspension system of 13, wherein a revolving joint between the two yokes comprises a brake device.

15. The suspension system of claim 13, wherein the yoke members of the two yokes have identical shapes.

16. The suspension system of 15, wherein a revolving joint between the two yokes comprises a brake device.

17. The suspension system of 16, wherein the suspension system further comprises a lamp body.

18. The suspension system of 13, wherein the suspension system further comprises a lamp body.

19. The suspension system of 1, wherein the suspension system further comprises a lamp body.

* * * * *